United States Patent
Hong et al.

(10) Patent No.: US 8,377,124 B2
(45) Date of Patent: Feb. 19, 2013

(54) TWO-ELEMENT SYSTEM TO PROVIDE AN EASE OF ACCOMMODATION WITH VARIABLE-SPHERICAL ABERRATION CONTROL

(75) Inventors: Xin Hong, Arlington, TX (US); Xiaoxiao Zhang, Fort Worth, TX (US)

(73) Assignee: Novartis AG, Basel (CH)

( * ) Notice: Subject to any disclaimer, the term of this patent is extended or adjusted under 35 U.S.C. 154(b) by 402 days.

(21) Appl. No.: 12/242,270

(22) Filed: Sep. 30, 2008

(65) Prior Publication Data

US 2009/0088841 A1 Apr. 2, 2009

Related U.S. Application Data

(60) Provisional application No. 60/976,947, filed on Oct. 2, 2007.

(51) Int. Cl.
*A61F 2/16* (2006.01)
(52) U.S. Cl. ............ 623/6.37; 623/6.32; 623/6.34; 623/6.49; 623/6.46
(58) Field of Classification Search ......... 623/6.32–6.37
See application file for complete search history.

(56) References Cited

U.S. PATENT DOCUMENTS

| | | | |
|---|---|---|---|
| 3,305,294 A | 2/1967 | Alvarez | |
| 3,583,790 A | 6/1971 | Baker | |
| 3,617,116 A | 11/1971 | Jones | |
| 4,994,082 A | 2/1991 | Richards et al. | |
| 2003/0045931 A1* | 3/2003 | Lang | 623/5.11 |
| 2003/0130732 A1* | 7/2003 | Sarfarazi | 623/6.13 |
| 2006/0030938 A1* | 2/2006 | Altmann | 623/6.37 |

FOREIGN PATENT DOCUMENTS

| | | |
|---|---|---|
| EP | 0 328 930 | 8/1989 |
| WO | WO 2005/084587 | 9/2005 |
| WO | WO 2006/118452 | 11/2006 |
| WO | WO 2007/015640 | 2/2007 |

* cited by examiner

*Primary Examiner* — David H Willse
*Assistant Examiner* — Tiffany Shipmon
(74) *Attorney, Agent, or Firm* — Jonathan E. Prejean

(57) ABSTRACT

In one aspect, the present invention provides a two-element ophthalmic lens in which a lateral shift of the elements relative to one another can cause a variation not only in a spherical power provided by the lens but also in spherical aberration exhibited by that lens. In some implementations, the thickness profiles of the two elements are designed such that the variation in spherical aberration is positively correlated with that of the spherical power of the lens.

8 Claims, 5 Drawing Sheets

TWO-ELEMENT SYSTEM TO PROVIDE AN EASE OF ACCOMMODATION WITH VARIABLE-SPHERICAL ABERRATION CONTROL

RELATED APPLICATIONS

This application claims priority under 35 USC §119 to U.S. provisional application Ser. No. 60/976,947, filed on Oct. 2, 2007.

BACKGROUND

The present invention relates generally to ophthalmic lenses, and more particularly to intraocular lenses (IOLs) that exhibit an accommodative optical power.

Intraocular lenses are routinely implanted in patients' eyes during cataract surgery to replace a clouded natural crystalline lens. The optical power of the natural crystalline lens can vary under the influence of the ciliary muscles to provide accommodation for viewing objects at different distances from the eye. Many IOLs, however, provide a monofocal power with no provision for accommodation, or a bifocal power with a limited degree of accommodation (typically referred to as "pseudoaccommodation). Accommodative IOLs are also known that can provide enhanced accommodation relative to that provided by monofocal or bifocal lenses. Many of such IOLs, however, employ a complex set of optical elements. Further, such IOLs do not generally take into account the role of aberrations as the lens provides accommodation for viewing objects at varying distances.

Hence, there is still a need for improved IOLs, and particularly for improved accommodative IOLs.

SUMMARY

In one aspect, the present invention provides an ophthalmic lens, e.g., an IOL, that provides an optic having two optical elements disposed in tandem along an optical axis, where at least one of those elements is capable of lateral movement relative to the other along a direction substantially transverse to the optical axis. The optical elements are configured such that the lateral movement causes a variation in an optical power provided by the optic as well as a variation in spherical aberration exhibited by the optic.

The spherical aberration can change as a function of the lateral displacement of the elements relative to one another. By way of example, in some cases the spherical aberration increases, e.g., linearly, as a function of increase in the lateral displacement. In many cases, the variation of spherical aberration as a function of lateral shift between the elements is positively related to the variation of the spherical optical power as a function of that shift (e.g., both the optical power and the spherical aberration can increase linearly with lateral displacement of the elements relative to one another).

In a related aspect, one of said elements exhibits a thickness profile $t_1(x,y)$, defined in accordance with the following relation:

$$t_1(x, y) = a\left(xy^2 + \frac{1}{3}x^3\right) + b\left(xy^4 + \frac{1}{5}x^5\right) + cx^3y^2$$

wherein x,y,z denote a Cartesian coordinate system formed by mutually orthogonal x,y, and z-axes, where the optical axis is along the z-axis, and wherein a,b,c are adjustable parameters. The other optical element can have a thickness profile $t_2(x,y)$ that is related to the thickness profile $t_1(x,y)$ in accordance with the following relation:

$$t_2(x,y) = -t_1(x,y)$$

In some implementations, the value of the parameter a,b, and c can be, respectively, in a range of about $$\frac{2.5}{\Delta n} (D/mm)$$

to about $$\frac{12.5}{\Delta n} (D/mm);$$

in a range of about $$\frac{-3.3}{32\Delta n} (D/mm^3)$$

to about $$\frac{2}{32\Delta n} (D/mm^3);$$

and $c = \frac{2}{3}b$, wherein $\Delta n$ denotes the difference between the refractive index of the material forming the optic and that of the surrounding medium, and (D/mm) denotes a unit of diopters per millimeter, and (D/mm³) denotes a unit of diopters per millimeter cubed.

In yet another aspect, an ophthalmic lens (e.g., an IOL) is disclosed that includes an anterior optical element and a posterior optical element, where the elements are capable of lateral movement relative to one another. The optical elements exhibit thickness profiles adapted such that a lateral movement of the elements relative to one another causes a variation in at least one aberration (e.g., spherical aberration) exhibited by a combination of those elements.

Further understanding of various aspects of the invention can be obtained by reference to the following detailed description in conjunction with the associated drawings, which are discussed briefly below.

DETAILED DESCRIPTION

The embodiments of the present invention generally provide ophthalmic lenses, and methods for their manufacturing and use, that provide an accommodative spherical optical power as well as an adjustable spherical aberration. In some embodiments, the lens (e.g., an IOL) can be formed as a two-element optical system whose power and one or more higher-order aberrations can be controlled by adjusting lateral shifts between those elements. In many implementations, the thickness profiles of the two elements are designed such that a lateral shift of the elements relative to one another in a direction transverse to the optical axis can vary not only the combined spherical power of the two elements but also spherical aberration exhibited by a combination of those elements. Such a lens can have a variety of applications in accommodative refractive correction and/or static aberrations corrections. By way of example, such an IOL can ease the accommodative burden of the ciliary muscles so as to achieve a visual clarity over a wide distance range with limited muscle movement. In static aberration correction, such a lens can be utilized to provide customized aberration corrections, via different lateral shifts of the elements, for different individuals. In many implementations, the spherical aberration is positively related to the magnitude of accommodation corresponding to the lens's spherical optical power.

In the embodiments that follow, various aspects of the invention are discussed in connection with intraocular lenses (IOLs). The teachings of the invention can also be applied to other ophthalmic lenses, such as contact lenses. The term "intraocular lens" and its abbreviation "IOL" are used herein interchangeably to describe lenses that are implanted into the interior of the eye to either replace the eye's natural lens or to otherwise augment vision regardless of whether or not the natural lens is removed. Intracorneal lenses and phakic intraocular lenses are examples of lenses that may be implanted in the eye without removal of the natural lens.

Figure 1A:
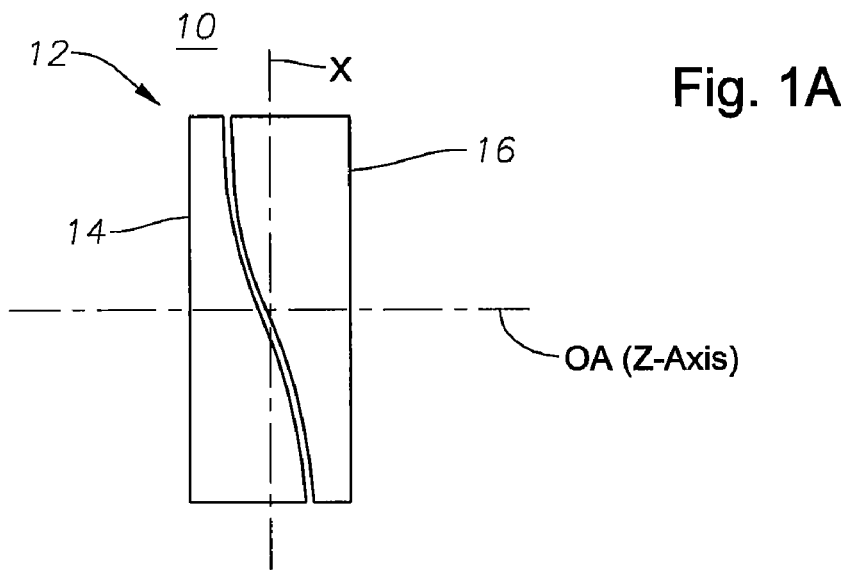
FIG. 1A is a schematic side view of an ophthalmic lens according to one embodiment of the invention having an optic formed of two optical elements that are movable laterally relative to one another.
Figure 1B:
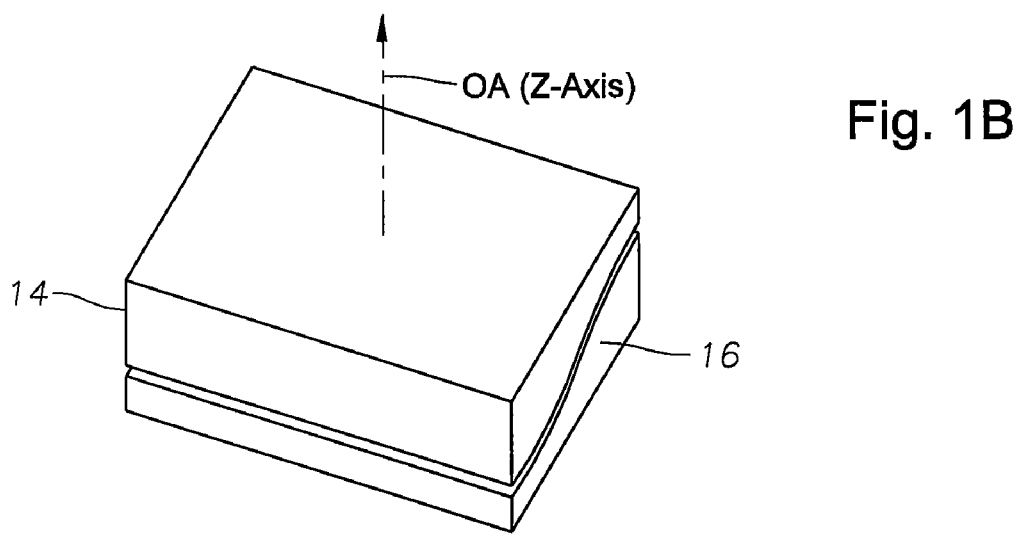
FIG. 1B is a schematic perspective view of the lens of FIG. 1A, FIG. 1C schematically depicts the thickness profile of one of the optical elements of the lens shown in FIGS. 1A and 1B (the other optical element has a similar thickness profile, but with an opposite sign), FIG. 2A schematically depicts an exemplary implementation of a two-element IOL according to one embodiment of the invention having two haptics that are connected via flexible hinges that allow their lateral movement relative to one another, FIG. 2B schematically depicts the haptics of the IOL shown in FIG. 2A and the flexible hinges connecting those haptics, FIG. 2C schematically depicts the hinges of the IOL of FIG. 2A once the IOL is implanted in the capsular bag of an eye, FIG. 3A schematically depicts another exemplary implementation of a two-element IOL according to the invention having two haptics that are connected by a plurality of flexible hinges such that the haptics, and consequently the optics, exhibit a lateral offset in a relaxed state of the hinges, FIG. 3B schematically shows the haptics depicted in FIG. 3A, and FIG. 3C schematically depicts the haptics shown in FIG. 3B once the IOL of FIG. 3A is implanted in the capsular bag of an eye.

FIGS. 1A and 1B depict a variable-power intraocular lens (IOL) 10 in accordance with one exemplary embodiment of the invention that includes an optic 12 comprising an anterior optical element 14 (herein also referred to as an anterior optic) and a posterior optical element 16 (herein also referred to as a posterior optic) that are disposed in tandem along an optical axis OA (herein depicted to extend along z-axis of an xyz coordinate system defined by mutually orthogonal x,y, and z axes). The anterior and posterior optical elements are configured to move relative to one another in a direction substantially transverse to the optical axis OA. More particularly, in this implementation, the posterior optical element remains fixed while the anterior optical element can be moved along the x-direction. In other implementations, the anterior optical element remains fixed while the posterior element is moved, or both elements can be moved. As discussed in more detail below, such a lateral shift of the optical elements relative to one another can vary not only the optical power provided by the optic 12 (i.e., the optical power provided by the combination of the optical elements 14 and 16), but also a spherical aberration exhibited by the optic (i.e., the spherical aberration exhibited by the combination of the optical elements 14 and 16).

Figure 1C:
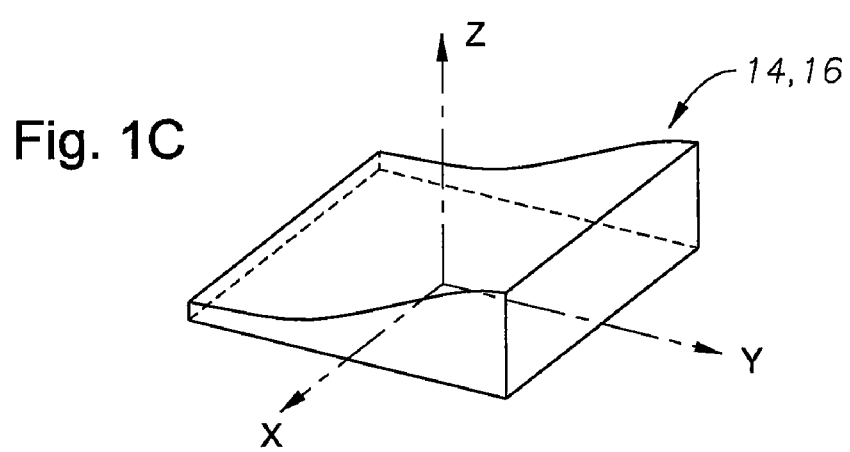

More specifically, as shown schematically in FIGS. 1A-1C, each of the optical elements 14 and 16 exhibits a non-uniform thickness profile. The non-uniform thickness profiles of the optical elements are designed so as to cooperatively cause a change in the optic's optical power as well as its spherical aberration via a lateral shift of the elements relative to one another. More specifically, in this exemplary implementation, the thickness profile ($t_1(x,y)$) of one of the elements (e.g., the thickness profile of the anterior optical element) and the thickness profile ($t_2(x,y)$) of the other element (e.g., the thickness profile of the posterior optical element) are defined in accordance with the following relation:

$$t_1(x,y) = -t_2(x,y) = t(x,y) \qquad \text{Eq. (1)}$$

where $t(x,y)$ is, in turn, defined in accordance with the following relation:

$$t(x, y) = a\left(xy^2 + \frac{1}{3}x^3\right) + b\left(xy^4 + \frac{1}{5}x^5\right) + cx^3y^2 \qquad \text{Eq. (2)}$$

wherein a, b, and c are adjustable parameters having opposite signs for $t_1$ and $t_2$.

To illustrate how the above thickness profiles can result in a change in spherical power of the optic 12 as well as its spherical aberration, consider a lateral shift of the optical elements relative to one another along the x-axis by a distance ($\Delta x$), e.g., characterized by a positive movement of the anterior element $$14 \text{ by} \left(\frac{\Delta x}{2}\right)$$

and a negative movement of the posterior element $$16 \text{ by} \left(-\frac{\Delta x}{2}\right).$$

The optical path difference (OPD), from which wavefronts can be determined, caused by the combination of the two elements as a function of x and y can then be defined by the following relation:

$$OPD \cong \frac{\partial t}{\partial x}\Delta x \Delta n \qquad \text{Eq. (3)}$$
$$= (a(x^2 + y^2) + b(x^4 + y^4) + 3cx^2y^2)\Delta x \Delta n$$

wherein $\Delta n$ denotes the difference between the index of refraction of the material from which the optical elements are formed (in this embodiment, the optical elements are assumed to be formed of the same material) and that of a medium surrounding those elements.

Generally, the parameters c and b can be selected independently based, e.g., on the design requirements of an IOL. However, by way of example, consider the case in which $$c = \frac{2}{3}b.$$

The optical path difference can then be defined by the following relation:

$$OPD = (a(x^2+y^2) + b(x^4+2x^2y^2+y^4))\Delta x \Delta n \quad \text{Eq. (4)}$$

By introducing a parameter $\rho$, which is equal to $(x^2+y^2)$, the above Equation (4) can be rewritten in the following form:

$$OPD = (a\rho^2 + b\rho^4)\Delta x \Delta n \quad \text{Eq. (5)}$$

The first term in the above relation (5) provides spherical optical power of the combination of the optical elements while the second term defines spherical aberration exhibited by the combination of those elements. The relation (5) shows that in this implementation both the spherical optical power and the spherical aberration vary linearly as a function of the lateral shift ($\Delta x$) between the two elements.

More generally, the variation of the spherical optical power and spherical aberration can be further understood by calculating the curvature of OPD as follows:

$$\text{Curvature}(OPD) = \left(\frac{\partial^2}{\partial x^2} + \frac{\partial^2}{\partial y^2}\right)\left(\frac{\partial t}{\partial x}\Delta x \Delta n\right) \quad \text{Eq. (6)}$$

$$= (4a + (12b + 6c)(x^2 + y^2))\Delta x \Delta n$$

$$= (4a + (12b + 6c)\rho^2)\Delta x \Delta n$$

where again the parameter $\rho$ is substituted for $(x^2+y^2)$,

The spherical aberration coefficient can then be calculated by applying the Laplacian operator $$\left(\text{i.e., } \frac{\partial^2}{\partial x^2} + \frac{\partial^2}{\partial y^2}\right)$$

to the curvature of the OPD (relation 6) as shown in the following relation (7):

$$\text{Spherical Aberration Coefficient} = \left(\frac{\partial^2}{\partial x^2} + \frac{\partial^2}{\partial y^2}\right)(\text{Curvature}(OPD)) \quad \text{Eq. (7)}$$

$$= \left(\frac{\partial^2}{\partial x^2} + \frac{\partial^2}{\partial y^2}\right)\left(\frac{\partial t}{\partial x}\Delta x \Delta n\right)$$

$$= (24b + 12c)\Delta x \Delta n$$

The above relation (7) shows that the spherical aberration exhibited by the combination of the optical elements 14 and 16 varies linearly as a function of relative lateral separation ($\Delta x$) between those elements. In this exemplary implementation, as shown by the above relation (6), the combined optical power of the two elements also varies linearly as a function of lateral separation between those elements. In fact, in this embodiment, both the optical power and the spherical aberration increase linearly as the lateral separation between the elements increases.

In other words, the spherical aberration of the lens 10 is positively related to its accommodative magnitude. Many studies of the human eye with a natural crystalline lens show that a similar effect is also present in the human eye: more spherical aberration in accommodative state than in the relaxed state. Hence, the lens 10 provides a similar variation of the spherical aberration as a function of increasing optical power.

In many implementations of the lens 10, the above parameters a, b and c are selected such that the lens would provide the following properties: for distance vision (e.g., for viewing objects at distances greater than about 2 m from the eye), the spherical aberration is minimal (e.g., it is less than about 0.06 D/mm$^2$); for near vision (e.g., for viewing objects at distances less than about 0.5 m from the eye) the spherical aberration is considerably larger (e.g., it is greater than about 0.33 D/mm$^2$) so as to enhance the depth-of-focus for viewing objects at a variety of distances; and from distance vision to near vision, the spherical aberration increases linearly to reduce required movement of ciliary muscles.

By way of example, in some cases, parameter a can be in a range of about $$\frac{2.5}{\Delta n}(D/mm)$$

to about $$\frac{12.5}{\Delta n}(D/mm);$$

parameter b can be in a range of about $$\frac{-3.3}{32\Delta n}(D/mm^3)$$

to about $$\frac{2}{32\Delta n}(D/mm^3);$$

$$\text{and } c = \frac{2}{3}b,$$

wherein $\Delta n$ denotes difference between the refractive index of the material forming the optic and that of the surrounding medium, and (D/mm) denotes a unit of diopters per millimeter. and (D/mm³) denotes a unit of diopters per millimeter cubed. In some cases, the index of refraction of the material forming the lens can be in a range of about 1.4 to about 1.6, and the index of refraction of the surrounding medium (e.g., aqueous humor of the eye) can be about 1.3.

Referring again to FIG. 1A-1C, in many implementations, the optical elements 14 and 16 are formed of a suitable biocompatible material. Some examples of such materials include, without limitation, soft acrylic, silicone, hydrogel or other biocompatible polymeric materials having a requisite index of refraction for a particular application of the lens. By way of example, the index of refraction of the material forming the optical elements can be in a range of about 1.4 to about 1.6 (e.g., the optic can be formed of a lens material commonly known as Acrysof® (a cross-linked copolymer of 2-phenylethyl acrylate and 2-phenylethyl methacrylate) having an index of refraction of 1.55). While in many embodiments, the optical elements 14 and 16 are formed of the same material, in some others, they can be formed of different materials with different indices of refraction. In the latter case, the above relations for the thickness profiles of the two optical elements can be appropriately scaled to account for the different in the indices of refraction of the two elements.

Figure 2A:
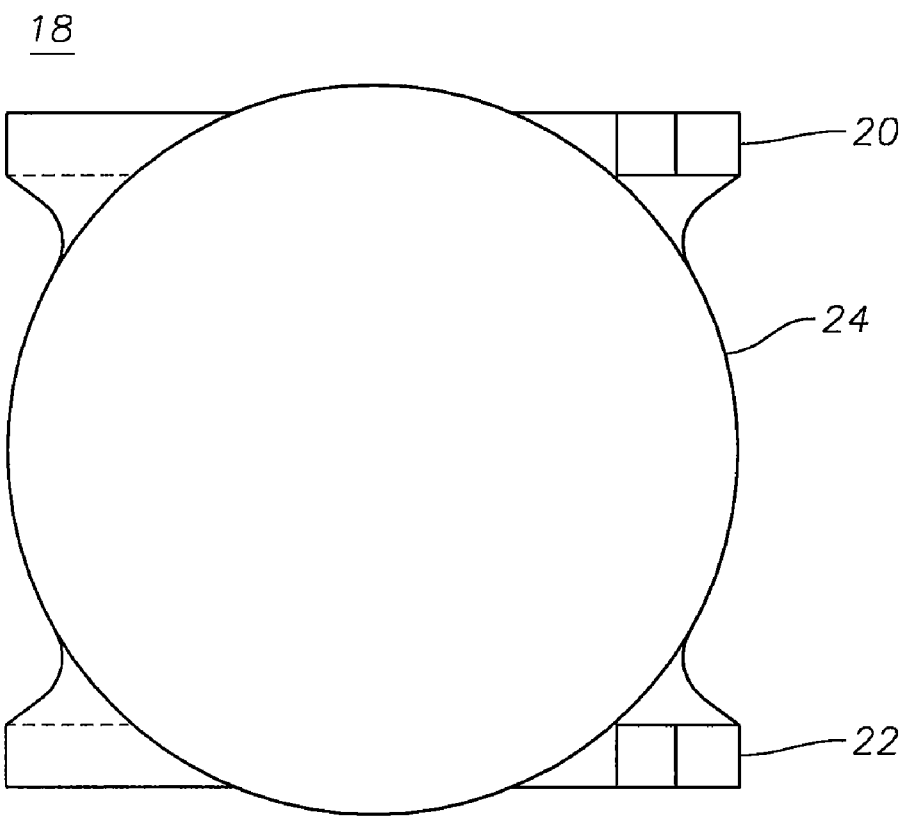
Figure 2B:
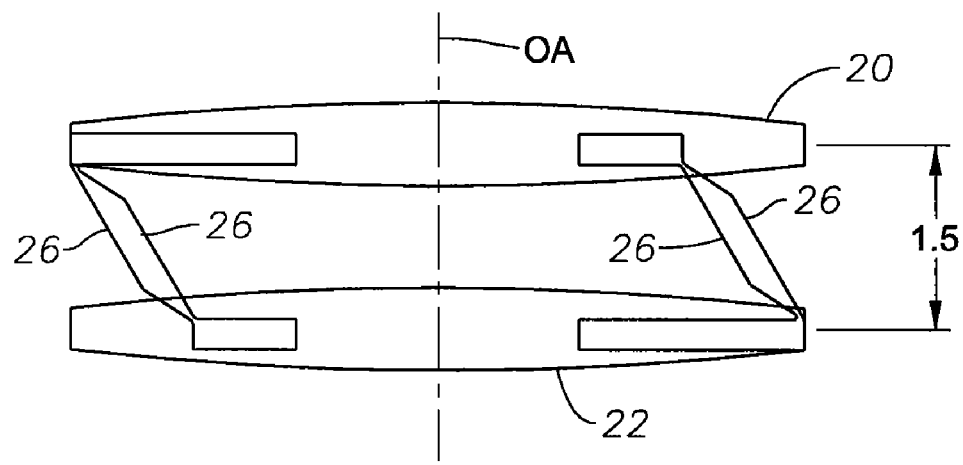
Figure 2C:
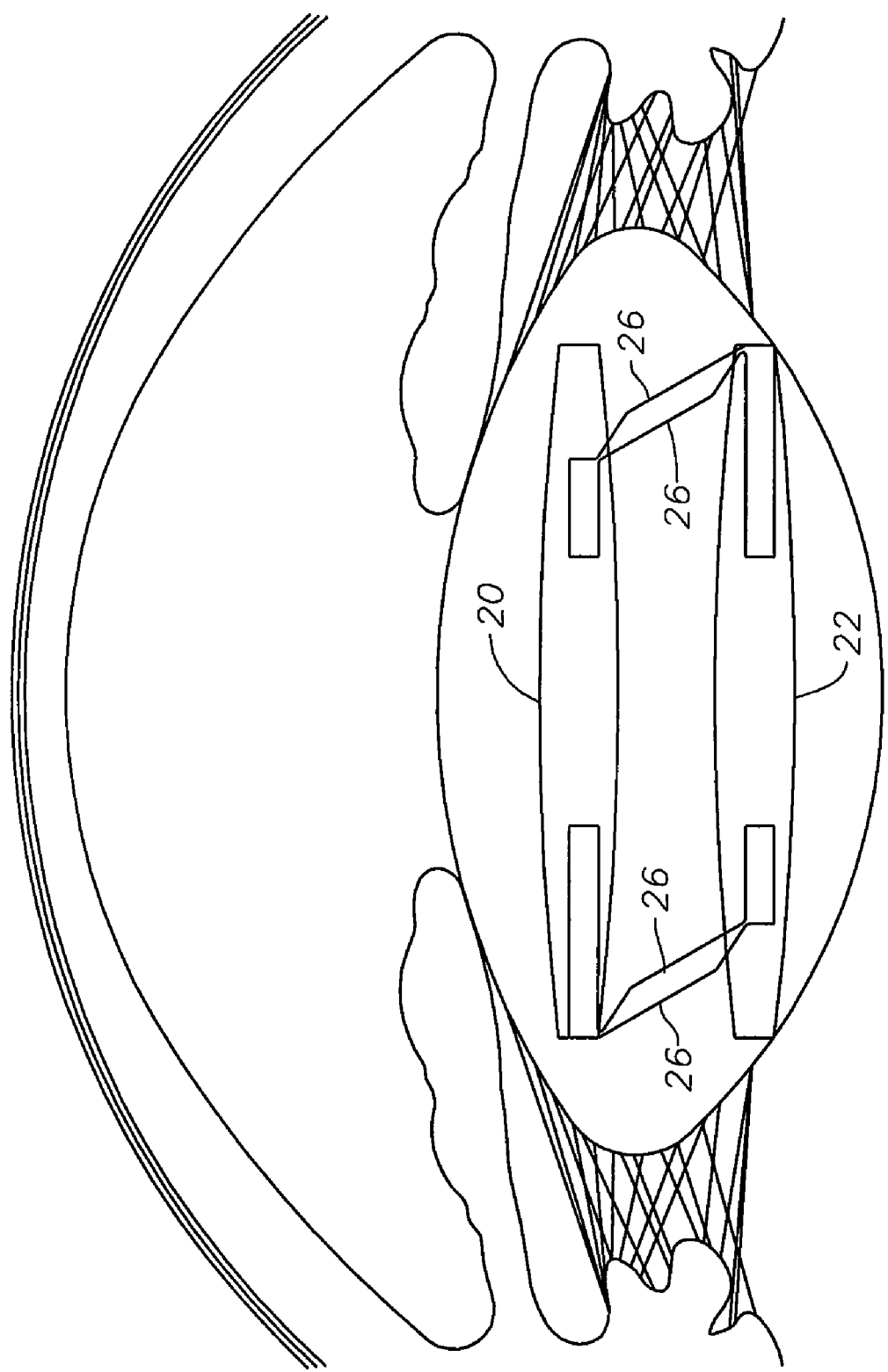

A two-element IOL according to the teachings of the invention can be implemented in a variety of ways. By way of example, with reference to FIGS. 2A and 2B, such an implementation of an IOL 18 includes two haptics 20 and 22, each of which is coupled to one of the two optical elements (e.g., only optical element 24 is shown, with the other optical element directly behind it) forming the lens (in this implementation the optical elements are separated from one another along an optical axis OA, e.g., by about 1.5 mm). The haptics are, in turn, coupled to one another via a plurality of flexible hinges 26 that allow lateral movement of the two haptics, and consequently that of the two optics, relative to one another (the haptics and the hinges can be formed, e.g., of suitable polymeric materials). In a relaxed state, the two haptics, and hence the two optics, have vanishing lateral offset relative to one another, with the offset increasing with increasing accommodation. By way of further illustration, as shown schematically in FIG. 2C, the IOL 18 can be implanted in the capsular bag of an eye, e.g., to replace a removed clouded natural lens. The accommodative force of the ciliary muscles on the capsular bag can cause a lateral motion of the haptics 20 and 22 (e.g., by an amount in a range of about 0.1 to about 0.5 mm), via the hinges 26, relative to one another, to increase the optical power of the IOL as well as spherical aberration exhibited by the IOL. As the muscles return to their relaxed state, the flexible hinges also return to their relaxed (equilibrium) state with a concomitant decrease in the offset between the optical elements and consequently a decrease in the optical power of the IOL.

Figure 3A:
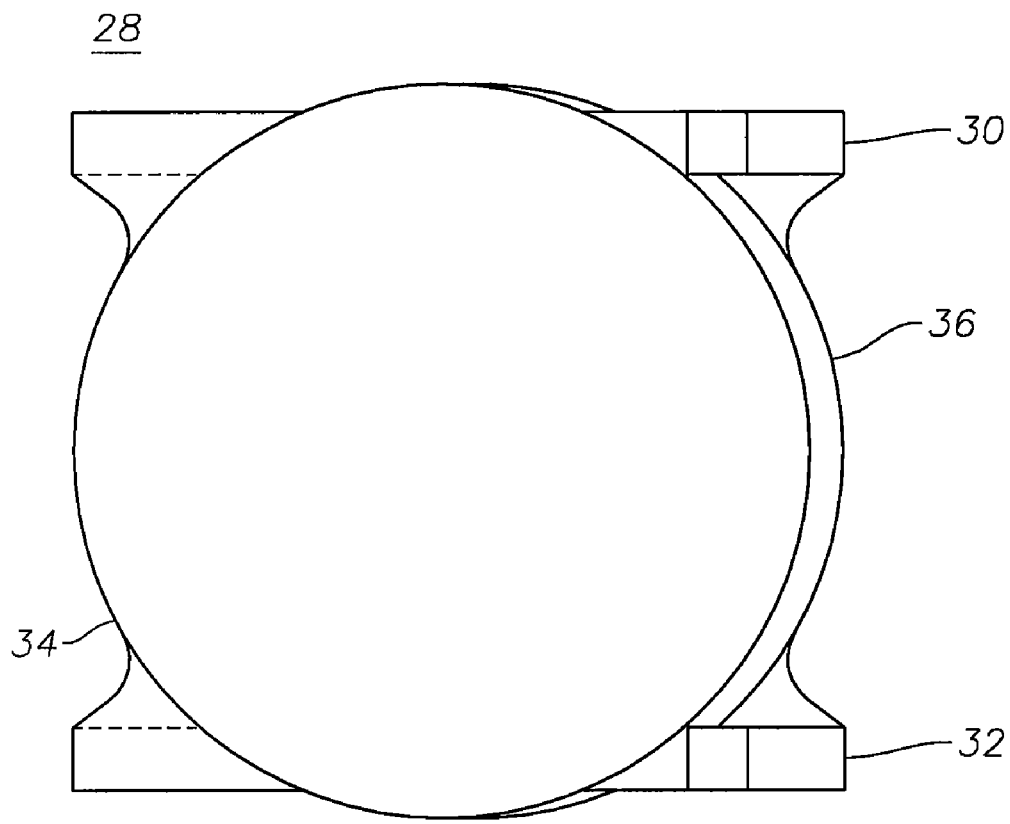
Figure 3B:
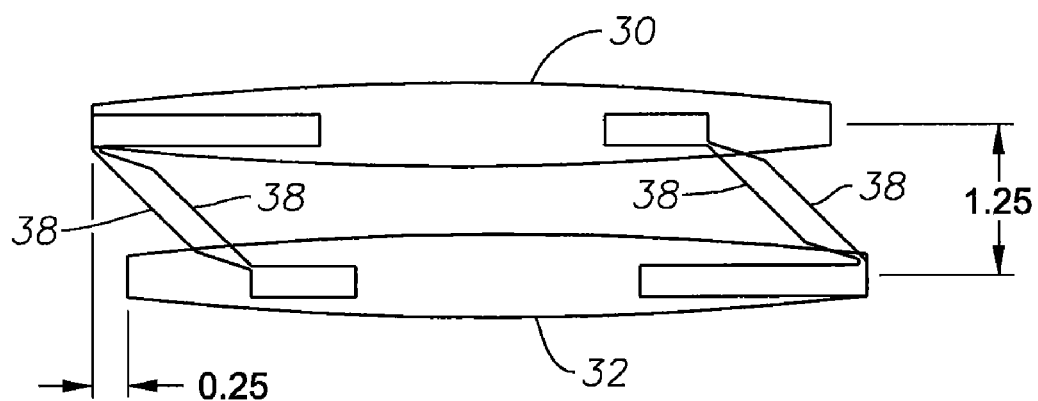
Figure 3C:
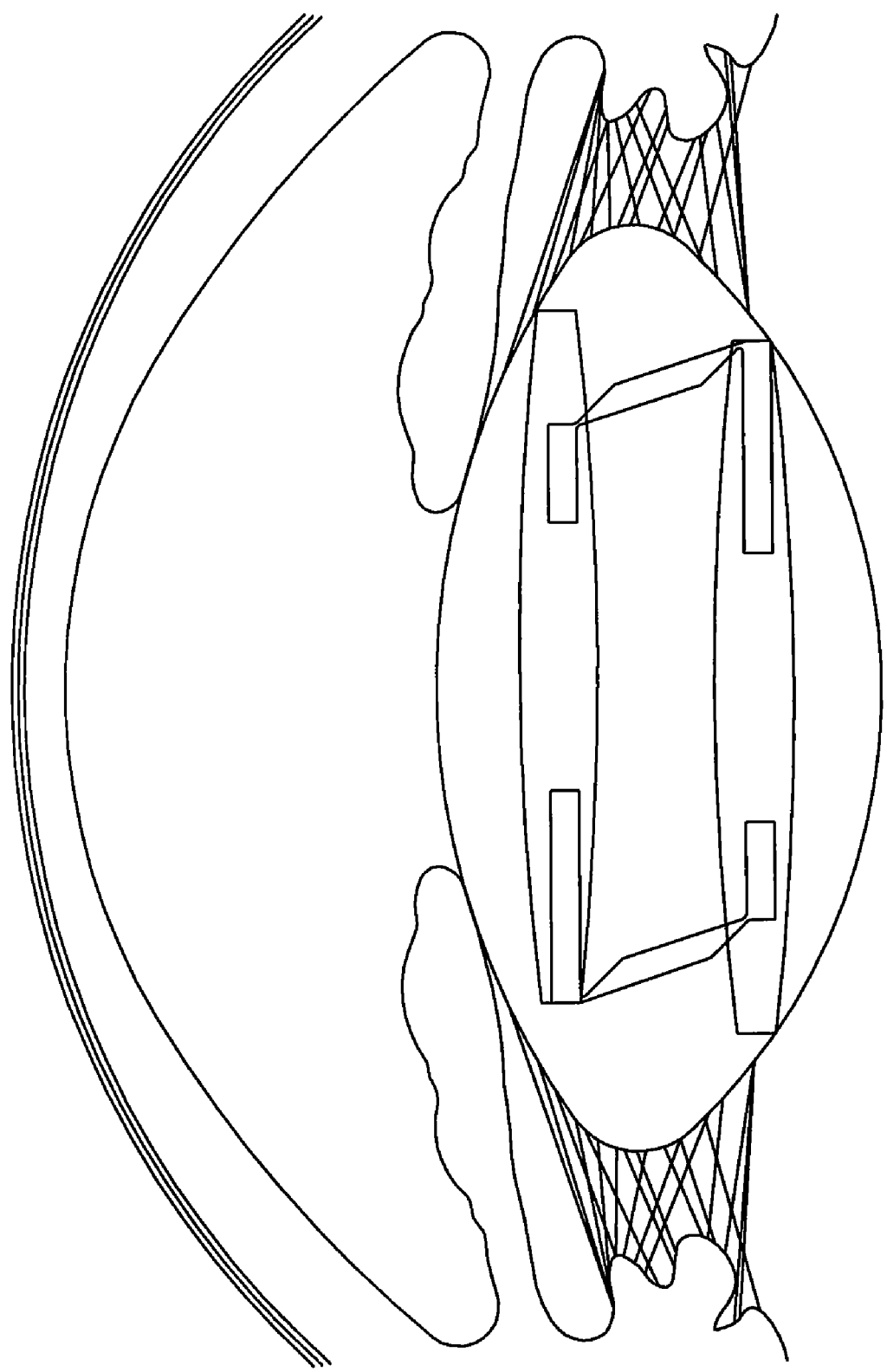

By way of another example, FIGS. 3A and 3B depict another implementation of a two-element IOL 28, which also includes two haptics 30 and 32, each attached to one the two optics 34 and 36, that are connected via a plurality of flexible hinges 38. Unlike the previous implementation, in a relaxed state the haptics are laterally offset relative to one another by a predefined amount (e.g., about 0.25 mm in this case) to provide a desired optical power and spherical aberration in the relaxed state. As shown schematically in FIG. 3C, again once the IOL 28 is implanted in the capsular bag of an eye, the hinges 38 can move laterally relative to one another under the influence of the ciliary muscles to vary the IOL's optical power as well as its spherical aberration for viewing objects at different distances.

In some applications, a lens according to the teachings of the invention can be used not as an accommodative lens, but rather as a lens providing a static optical power. In such cases, the lateral shift of the elements can be employed to adjust the optical power as well as a desired spherical aberration of the lens for a particular patient.

A variety of known manufacturing techniques can be employed to fabricate ophthalmic lenses (e.g., IOLs) in accordance with the teachings of the invention. For example, the two optics can be formed and then assembled, e.g., via a plurality of haptics and flexible hinges, along an optical axis.

Although embodiments have been described in detail herein, it should be understood that the description is by way of example only and is not to be construed in a limiting sense. It is to be further understood, therefore, that numerous changes in the details of the embodiments and additional embodiments will be apparent, and may be made by, persons of ordinary skill in the art having reference to this description. It is contemplated that all such changes and additional embodiments are within scope of the claims below.

What is claim is:

1. An IOL, comprising
an anterior optic and a posterior optic disposed about an optical axis,
at least two haptics each coupled to one of said optics,
a plurality of flexible hinges connecting said two haptics so as to allow lateral movement of the two haptics relative to one another, thereby causing a lateral movement of said optics relative to one another, the flexible hinges having a parallelogram-shaped cross-section in a plane defined by the optical axis and a direction of the lateral movement, the parallelogram-shaped cross-section having a major diagonal extending between opposite corners connected to the haptics at hinge joints and a minor diagonal shorter than the major diagonal, wherein the flexible hinges flex only at the hinge joints;
wherein said optical element are configured such that said lateral movement causes a change in a combined optical power provided by said optics as well as spherical aberration exhibited by a combination of said optics.

2. The IOL of claim 1, wherein said haptics are configured such that said lateral movement is substantially transverse to said optical axis.

3. The ophthalmic lens of claim 1, wherein said elements are configured such that the spherical aberration increases as the optical power increases.

4. The ophthalmic lens of claim 1, wherein said spherical aberration changes as a function of a displacement associated with said lateral movement.

5. The ophthalmic lens of claim 3, wherein said spherical aberration increases as said displacement increases.

6. The ophthalmic lens of claim 5, wherein said spherical aberration increases linearly as a function of increase in said displacement.

7. The ophthalmic lens of claim 1, wherein one of said elements exhibits a thickness profile $t_1(x,y)$ defined in accordance with the following relation:

$$t_1(x, y) = a\left(xy^2 + \frac{1}{3}x^3\right) + b\left(xy^4 + \frac{1}{5}x^5\right) + cx^3y^2$$

wherein x, y, z denote a Cartesian coordinate system formed by mutually orthogonal x, y, and z-axes, where the optical axis is along the z-axis, and wherein a, b, c are adjustable parameters, and wherein the other element exhibits a thickness $t_2(x,y)$ defined in accordance with the following relation:

$$t_2(x,y)=-t_1(x,y).$$

8. The ophthalmic lens of claim 7, wherein a is in a range of about $$\frac{2.5}{\Delta n}(Diopters/mm)$$

to about $$\frac{12.5}{\Delta n}(Diopters/mm);$$

b is in a range of about $$\frac{-3.3}{32\Delta n}(Diopters/mm^3)$$

to about $$\frac{2}{32\Delta n}(Diopters/mm^3);$$

and $c = \frac{2}{3}b$, and wherein $\Delta n$ denotes difference between the refractive index of the material forming the optic and that of the surrounding medium.

* * * * *